United States Patent
Heil, Jr. et al.

(10) Patent No.: US 6,584,363 B2
(45) Date of Patent: *Jun. 24, 2003

(54) IMPLANTABLE LEAD WITH DISSOLVABLE COATING FOR IMPROVED FIXATION AND EXTRACTION

(75) Inventors: Ronald W. Heil, Jr., Roseville, MN (US); John E. Heil, White Bear Lake, MN (US); Randy Westlund, Minneapolis, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/906,571

(22) Filed: Jul. 16, 2001

(65) Prior Publication Data

US 2002/0045926 A1 Apr. 18, 2002

Related U.S. Application Data

(63) Continuation of application No. 09/280,096, filed on Mar. 29, 1999, now Pat. No. 6,304,786.

(51) Int. Cl.$^7$ .................................................. A61N 1/05
(52) U.S. Cl. ...................................................... 607/126
(58) Field of Search ..................................... 607/1–156

(56) References Cited

U.S. PATENT DOCUMENTS

| | | | |
|---|---|---|---|
| 3,279,996 A | 10/1966 | Long, Jr. et al. | 167/82 |
| 3,699,956 A | 10/1972 | Kitrilakis et al. | 128/348 |
| 4,073,999 A | 2/1978 | Bryan et al. | 428/311 |
| 4,444,206 A | 4/1984 | Gold | 128/784 |
| 4,506,680 A | 3/1985 | Stokes | 128/786 |
| 4,577,642 A | 3/1986 | Stokes | 128/786 |
| 4,606,118 A | 8/1986 | Cannon et al. | 29/825 |
| 4,628,944 A | 12/1986 | MacGregor et al. | 128/785 |
| 4,711,251 A | 12/1987 | Stokes | 128/784 |
| 4,819,661 A | 4/1989 | Heil, Jr. et al. | 128/786 |
| 4,819,662 A | 4/1989 | Heil, Jr. et al. | 128/786 |
| 4,953,564 A | 9/1990 | Berthelsen | 128/784 |
| 4,972,848 A | 11/1990 | DiDomenico et al. | 128/785 |
| 5,002,067 A | 3/1991 | Berthelsen et al. | 128/786 |
| 5,003,992 A | 4/1991 | Holleman et al. | 128/785 |
| 5,009,229 A | 4/1991 | Grandjean et al. | 128/419 |

(List continued on next page.)

FOREIGN PATENT DOCUMENTS

| | | | |
|---|---|---|---|
| EP | 0784995 | 12/1996 | A61N/1/05 |
| EP | 0795343 | 2/1997 | A61N/1/05 |
| GB | 2240721 | 8/1991 | A61N/1/05 |

OTHER PUBLICATIONS

Howes, E.L., et al., "Retardation of Wound Healing by Cortisone", *Surgery*, vol. 28, No. 2, (Aug., 1950).

*Primary Examiner*—Scott M. Getzow
(74) *Attorney, Agent, or Firm*—Schwegman, Lundberg, Woessner & Kluth, P.A.

(57) ABSTRACT

A cardiac rhythm management system provides an endocardial cardiac rhythm management lead with an at least partially dissolvable coating at least partially on insulating portions of the lead body at or near its distal end. Upon dissolution, the coating promotes tissue ingrowth to secure the lead in place within fragile vascular structures or elsewhere. Dissolution of one such coating releases a therapeutic agent, such as a steroid that modifies the fibrotic scar tissue content of tissue ingrowth, such that the resulting bond between the tissue and the lead is weak, so that the lead can be easily extracted if desired. One such lead includes an insulating elongate body carrying at least. The lead also includes an at least partially dissolvable coating on an insulating portion of the peripheral distal lead surface. The coating provides one or more of a rough surface, a porous surface, or a swollen surface after being exposed to an aqueous substance.

59 Claims, 6 Drawing Sheets

U.S. PATENT DOCUMENTS

| | | | |
|---|---|---|---|
| 5,020,544 A | 6/1991 | Dahl et al. | 128/784 |
| 5,092,332 A | 3/1992 | Lee et al. | 128/642 |
| 5,103,837 A | 4/1992 | Weidtich et al. | 128/784 |
| 5,300,108 A | 4/1994 | Rebell et al. | 607/127 |
| 5,324,324 A | 6/1994 | Vachon et al. | 607/120 |
| 5,350,419 A | 9/1994 | Bendel et al. | 607/132 |
| 5,514,173 A | 5/1996 | Rebell et al. | 607/127 |
| 5,545,206 A | 8/1996 | Carson | 607/126 |
| 5,755,762 A | 5/1998 | Bush | 607/122 |
| 5,776,178 A | 7/1998 | Pohndorf et al. | 607/127 |
| 5,837,007 A | 11/1998 | Altman et al. | 604/127 |
| 5,861,023 A | 1/1999 | Vachon | 607/121 |
| 5,902,329 A | 5/1999 | Hoffmann et al. | 607/121 |
| 5,931,862 A | 8/1999 | Carson | 607/120 |

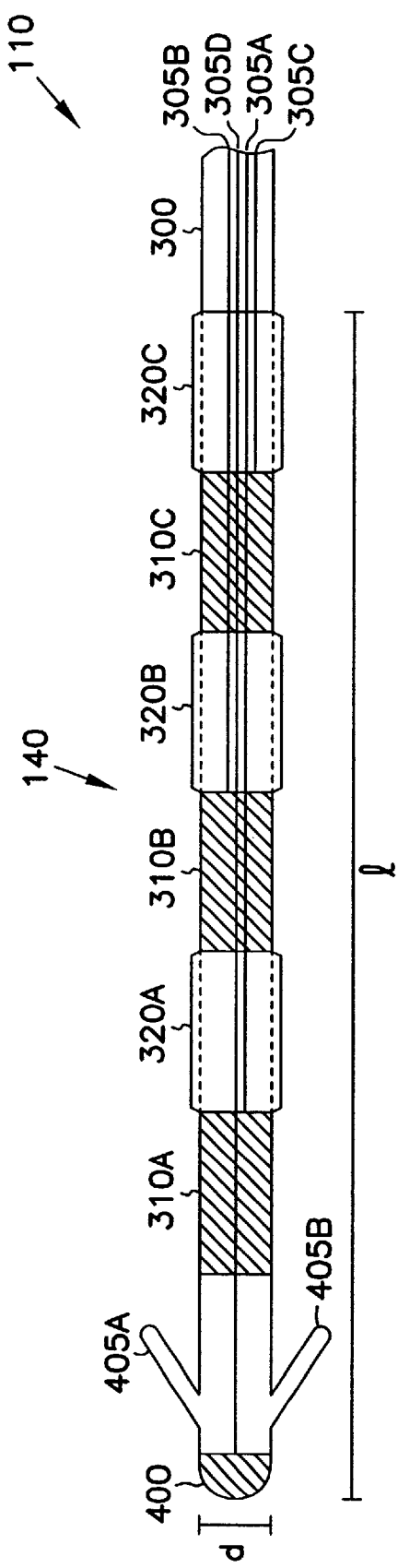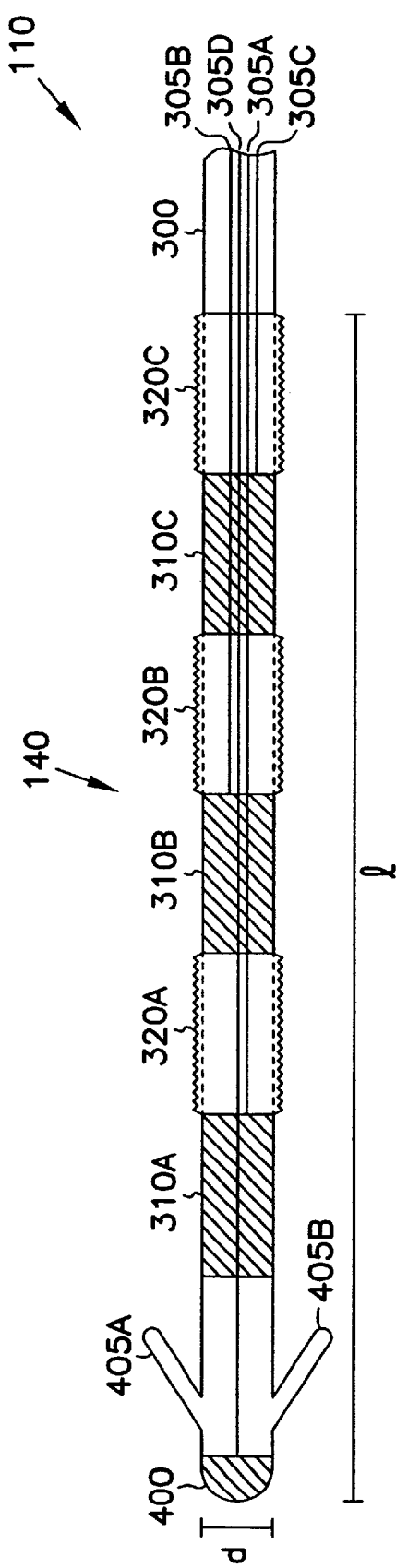

IMPLANTABLE LEAD WITH DISSOLVABLE COATING FOR IMPROVED FIXATION AND EXTRACTION

CROSS REFERENCE TO RELATED APPLICATIONS

This application is a continuation of U.S. patent application Ser. No. 09/280,096, filed on Mar. 29, 1999, now U.S. Pat. No. 6,304,786 the specification of which is incorporated herein by reference.

TECHNICAL FIELD

This invention relates generally to electrical leadwires and particularly, but not by way of limitation, to a cardiac rhythm management system providing an endocardial cardiac rhythm management lead with an at least partially dissolvable coating on at least portions of an insulating lead body for improved fixation and extraction.

BACKGROUND

When functioning properly, the human heart maintains its own intrinsic rhythm, and is capable of pumping adequate blood throughout the body's circulatory system. However, some people have irregular cardiac rhythms, referred to as cardiac arrhythmias. Such arrhythmias result in diminished blood circulation. One mode of treating cardiac arrhythmias uses drug therapy. Drugs are often effective at restoring normal heart rhythms. However, drug therapy is not always effective for treating arrhythmias of certain patients. For such patients, an alternative mode of treatment is needed. One such alternative mode of treatment includes the use of a cardiac rhythm management system. Such systems are often implanted in the patient and deliver therapy to the heart.

Cardiac rhythm management systems include, among other things, pacemakers, also referred to as pacers. Pacers deliver timed sequences of low energy electrical stimuli, called pace pulses, to the heart, such as via a transvenous leadwire or catheter (referred to as a "lead") having one or more electrodes disposed in or about the heart. Heart contractions are initiated in response to such pace pulses (this is referred to as "capturing" the heart). By properly timing the delivery of pace pulses, the heart can be induced to contract in proper rhythm, greatly improving its efficiency as a pump. Pacers are often used to treat patients with bradyarrhythmias, that is, hearts that beat too slowly, or irregularly.

Cardiac rhythm management systems also include cardioverters or defibrillators that are capable of delivering higher energy electrical stimuli to the heart. Defibrillators are often used to treat patients with tachyarrhythmias, that is, hearts that beat too quickly. Such too-fast heart rhythms also cause diminished blood circulation because the heart isn't allowed sufficient time to fill with blood before contracting to expel the blood. Such pumping by the heart is inefficient. A defibrillator is capable of delivering an high energy electrical stimulus that is sometimes referred to as a defibrillation countershock. The countershock interrupts the tachyarrhythmia, allowing the heart to reestablish a normal rhythm for the efficient pumping of blood. In addition to pacers, cardiac rhythm management systems also include, among other things, pacer/defibrillators that combine the functions of pacers and defibrillators, drug delivery devices, and any other systems or devices for diagnosing or treating cardiac arrhythmias.

One aspect of typical cardiac rhythm management systems is providing an appropriate endocardial lead coupling an implantable cardiac rhythm management device to the heart for sensing intrinsic electrical heart activity signals and/or delivering electrical therapy such as pacing stimulations or defibrillation countershocks. In conventional cardiac rhythm management systems, the lead typically includes a distal electrode that is transvenously guided into the right atrium or right ventricle. The electrode is carefully positioned to contact adjacent cardiac tissue for sensing and/or providing therapy. The preferred location provides adequate amplitude sensed intrinsic electrical heart activity signals and low threshold energy requirements for effectively delivering pacing and/or defibrillation therapy. To ensure that the electrode's location does not change over time in spite of continuous heart contractions, a fixation device may be used to anchor the distal end of the leadwire in position within the heart.

Even if the position of the electrode is stabilized, stimulation thresholds may vary over time as a result of interactions between the electrode and the adjacent tissue. Fibrotic scar tissue may form during the recovery and healing process as the body reacts to the presence of the electrode. The growth of fibrotic tissue results in chronic stimulation energy thresholds that exceed the acute energy thresholds obtained immediately after implant. As a result, higher stimulation energies are required, thereby shortening the usable life of the battery-powered implantable cardiac rhythm management device. By providing a steroid at the electrode and/or its associated fixation device, modified fibrotic tissue is formed and lower chronic stimulation thresholds are obtained, as disclosed in Heil, Jr. et al., U.S. Pat. No. 4,819,661, which is assigned to the assignee of the present application, and which is incorporated herein by reference in its entirety.

Use of a fixation device to anchor the lead typically obtains consistent chronic sensing and stimulation thresholds, but such fixation devices complicate removal of the lead such as, for example, in the event of an infection or lead failure. For example, removing a lead with a corkscrew or barb fixation device risks damage to the surrounding tissue to which the fixation device is firmly attached. Where such surrounding tissue is fibrotic scar tissue resulting from lead placement and fixation in conjunction with the normal healing process, separation of the lead from the surrounding scar tissue is even more difficult because the lead will likely have become firmly incorporated within the body. Moreover, many such fixation devices are adapted only for securing the distal tip of the lead; they may not adequately secure ring electrodes that are disposed at a slight distance away from the distal tip of the lead. Furthermore, most conventional fixation techniques are directed toward anchoring leads in the right side of the heart. Such techniques may not be as well suited for anchoring leads elsewhere. Thus, there is a need for providing a cardiac rhythm management lead that is capable of both adequate fixation and removal. There is also a need for providing a cardiac rhythm management lead that is capable of placement and fixation in other regions of the heart, such as within fragile vascular structures.

SUMMARY

This document describes, among other things, a cardiac rhythm management system providing an endocardial cardiac rhythm management lead with an at least partially dissolvable coating on at least portions of the lead body at or near its distal end, which promotes tissue ingrowth to secure the lead in place within fragile vascular structures or elsewhere. In one embodiment, dissolution of the coating releases a therapeutic agent. In a further embodiment, the therapeutic agent includes a steroid that modifies the fibrotic scar tissue component of tissue ingrowth, such that the resulting bond between the tissue and the lead is weak, such that the lead can be easily extracted if desired.

In one embodiment, the lead includes an insulating elongate body having a proximal and a distal end and a peripheral surface. At least one elongate electrical conductor, having a proximal end and a distal end, is carried within the elongate body. The conductor extends longitudinally along substantially the entire length between the proximal and distal ends of the elongate body. At least one electrode is located at or near the distal end of the elongate body. The electrode is coupled to the distal end of the conductor. The lead also includes an at least partially dissolvable coating on at least portions of the insulating peripheral surface at or near the distal end of the elongate body. The coating provides at least one of a rough surface, a porous surface, and a swollen surface after being exposed to an aqueous substance. Other aspects of the invention will be apparent on reading the following detailed description of the invention and viewing the drawings that form a part thereof.

BRIEF DESCRIPTION OF THE DRAWINGS

In the drawings, like numerals describe substantially similar components throughout the several views. Like numerals having different letter suffixes represent different instances of substantially similar components.

FIG. 4A is a schematic drawing illustrating generally another embodiment of portions of a lead.

FIG. 4B is a schematic drawing illustrating the portions of the lead of FIG. 4A after expc are to an aqueous substance.

DETAILED DESCRIPTION

Figure 1:
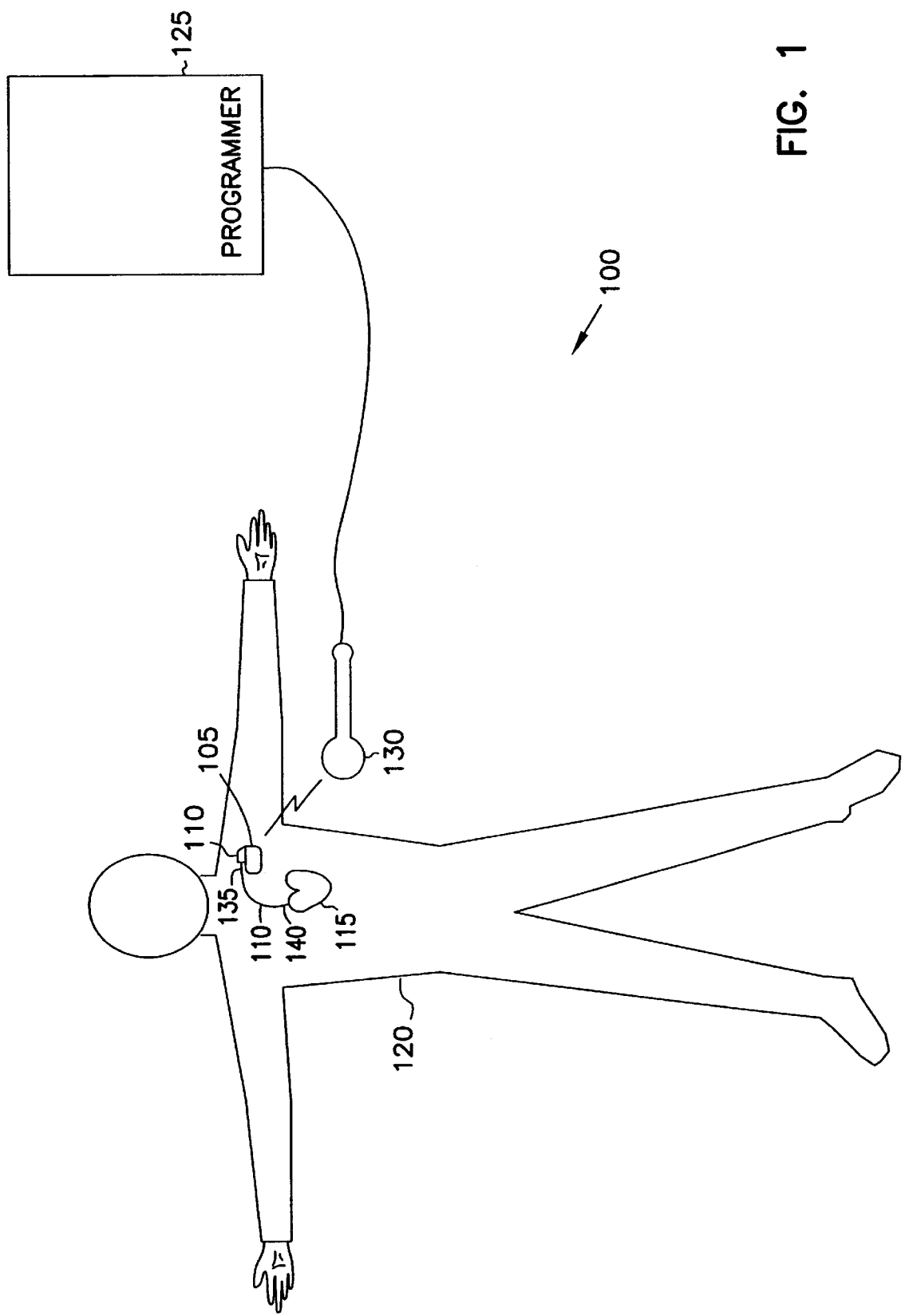
FIG. 1 is a schematic drawing illustrating generally one embodiment of portions of a cardiac rhythm management system and one environment in which it is used.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description is, therefore, not to be taken in a limiting sense, and the scope of the present invention is defined by the appended claims and their equivalents. In the drawings, like numerals describe substantially similar components throughout the several views. Like numerals having different letter suffixes represent different instances of substantially similar components.

General Overview

This document describes, among other things, a cardiac rhythm management system providing an endocardial cardiac rhythm management lead with an at least partially dissolvable coating on at least portions of an insulating lead body, for improved fixation and extraction.

FIG. 1 is a schematic drawing illustrating generally, by way of example, but not by way of limitation, one embodiment of portions of a cardiac rhythm management system 100 and one environment in which it is used. In FIG. 1, system 100 includes an implantable cardiac rhythm management device 105, which is coupled via an intravascular endocardial lead 110 to a heart 115 of a human or other patient 120. System 100 also includes an external programmer 125 providing wireless communication with device 105, such as by using a telemetry device 130. Lead 110 includes a proximal end 135, which is coupled to device 105, and a distal end 140, which is coupled on or about one or more portions of heart 115.

Figure 2:
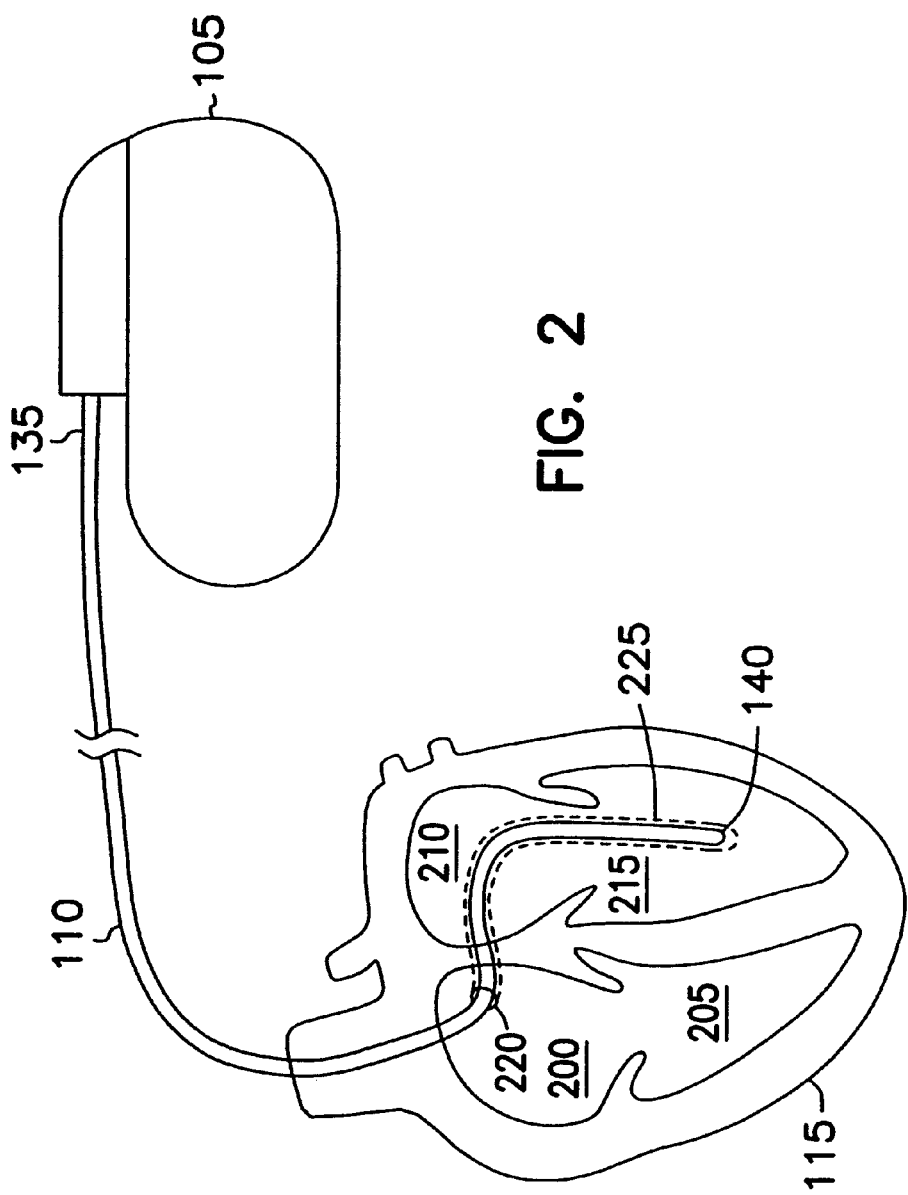
FIG. 2 is a schematic drawing illustrating generally one embodiment of a disposition of distal portions of a lead in a coronary sinus and/or a great cardiac vein.

FIG. 2 is a schematic drawing illustrating generally, by way of example, but not by way of limitation, one embodiment of an exemplary disposition of distal portions of lead 110. FIG. 2 illustrates chambers of heart 115, including a right atrium 200, a right ventricle 205, a left atrium 210, and a left ventricle 215. In the embodiment illustrated in FIG. 2, distal end 140 of lead 110 is transvenously guided into right atrium 200, through a coronary sinus 220, and into a great cardiac vein 225. This example disposition of lead 110 is useful for delivering pacing and/or defibrillation energy to the left side of heart 115, such as for treatment of congestive heart failure (CHF) or other cardiac disorders requiring therapy delivered to the left side of heart 115. Other possible dispositions of distal portions of endocardial lead 110 include insertion into right atrium 200 and/or right ventricle 205, or transarterial insertion into the left atrium 210 and/or left ventricle 215.

Figure 3A:
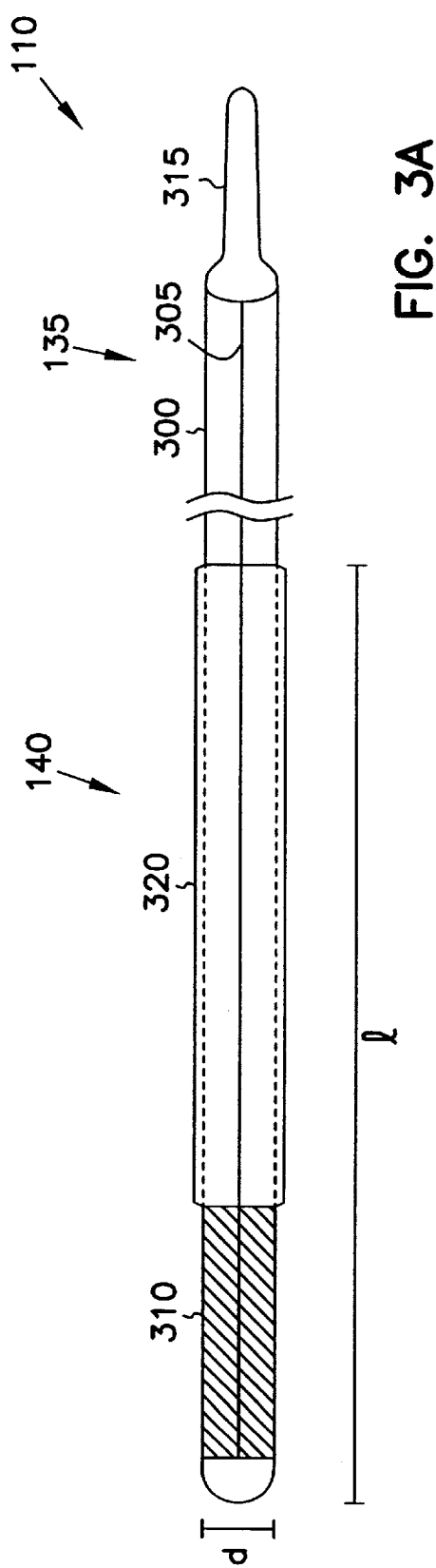
FIG. 3A is a schematic drawing illustrating one embodiment of portions of a lead.

FIG. 3A is a schematic drawing illustrating generally, by way of example, but not by way of limitation, one embodiment of portions of lead 110, including its distal end 140 and its proximal end 135. In this embodiment, intravascular endocardial lead 110 includes a biocompatible flexible insulating elongate body 300 (e.g., including a polymer such as medical grade silicone rubber) for translumenal (i.e., transvenous or transarterial) insertion and access within a living organism such as patient 120. In one embodiment, slender elongate body 300 is tubular and has a peripheral outer surface of diameter d that is small enough for translumenal insertion into coronary sinus 220 and/or great cardiac vein 225. An elongate electrical conductor 305 is carried within insulating elongate body 300. Conductor 305 extends substantially along the entire length between the distal end 140 and proximal end 135 of lead 110, and this length is long enough for lead 110 to couple device 105, which is implanted pectorally, abdominally, or elsewhere, to desired locations within heart 115 for sensing intrinsic electrical heart activity signals or providing pacing/defibrillation-type therapy thereto. Elongate body 300 forms an insulating sheath covering around conductor 305. Conductor 305 is coupled to an electrode 310 at or near distal end 140 of elongate body 300. Conductor 305 is coupled to a connector 315 at or near proximal end 135 of elongate body 300. Device 105 includes a receptacle for receiving connector 315, thereby obtaining electrical continuity between electrode 310 and device 105.

Electrode 310, or at least a portion thereof, is not covered by the insulating sheath of elongate body 300. The embodiment of FIG. 3A includes a ring or ring-like electrode 310 that provides an exposed electrically conductive surface around all, or at least part of, the circumference of lead 110. In one embodiment, the exposed surface of electrode 310 is smooth. In another embodiment, the exposed surface of electrode 310 is not smooth, thereby allowing tissue ingrowth into interstitial spaces of electrode 310. In one example, electrode 310 is a coiled wire electrode that is wound around the circumferential outer surface of lead 110. Lead 110 also includes other configurations, shapes, and structures of electrode 310.

Lead 110 includes a biocompatible coating 320 on at least one insulating portion of the peripheral surface of elongate body 300 at or near distal end 140. In one embodiment, as illustrated in FIG. 3A, coating 320 extends circumferentially completely (or at least partially) around the tubular outer peripheral surface of lead 110. In the embodiment of FIG. 3A, coating 320 occupies one or more nonelectrode regions (i.e., insulating portions of the lead body) extending along a length l from the tip of distal end 140 of lead 110, where length l is approximately equal to a distance within coronary sinus 220 and great cardiac vein 140 into which distal end 140 of lead 110 is inserted. In a further embodiment, coating 320 also overlaps one or more portions of one or more electrodes, such as electrode 310, providing an insulating covering that reduces the exposed surface area of the electrode 310.

Figure 3B:
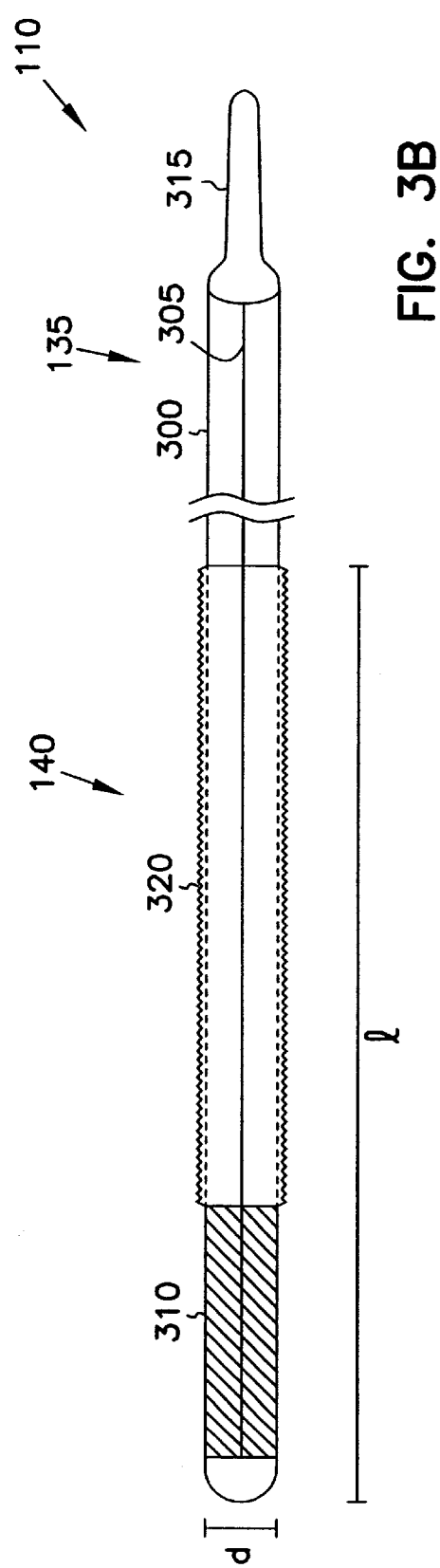
FIG. 3B is a schematic drawing illustrating the portions of the lead of FIG. 3A after exposure to an aqueous substance.

According to one aspect of the invention, coating 320 is at least partially dissolvable when exposed to an aqueous substance such as blood or bodily fluids. In one embodiment, coating 320 provides a substantially smooth low friction outer surface before dissolution of portions of coating 320. After being exposed to an aqueous substance, however, portions of coating 320 dissolve. According to one aspect of the present system, this dissolution initially makes distal end 140 of lead 110 more slippery, making it easier to insert into patient 120. After portions of coating 320 dissolve, remaining substrate portions of coating 320 provide a rough and/or porous surface (as illustrated in FIG. 3B) that promotes tissue ingrowth into resulting interstitial regions. Such tissue ingrowth anchors and/or secures lead 110 to adjacent cardiac tissue, such as within coronary sinus 220 and/or great cardiac vein 225, or elsewhere in or about heart 115. In one embodiment, portions of coating 320 undergo osmotic swelling after being exposed to the aqueous substance. This further assists in securing lead 110 within a vascular region such as, for example, within coronary sinus 220 and/or great cardiac vein 225. Thus, in one embodiment, coating 320 includes a plurality of substantially soluble particles dispersed in a substantially insoluble medium that is adhered to portions of elongate body 300 at or near distal end 140. When exposed to an aqueous environment, the substantially soluble particles dissolve, leaving behind a rough and/or porous surface that results in tissue ingrowth and/or osmotic swelling, which promotes lead fixation that is particularly well-suited for vascular structures.

In another embodiment, coating 320 includes a therapeutic agent such as, by way of example, but not by way of limitation, a drug, a steroid, a corticosteroid, an antibiotic, and/or an antirejection agent. In one example, the therapeutic agent is provided by the substantially soluble particles that are dispersed in the substantially insoluble medium. In one example, coating 320 includes substantially soluble particles of a steroid such as dexamethasone acetate. When coating 320 is exposed to an aqueous environment, the substantially soluble steroid elements dissolve, providing sustained release into the surrounding tissue. This delays local protein synthesis and tissue healing, which modifies the formation of normal fibrotic scar tissue during the recovery and healing process. As a result, a lesser amount of strongly-bound fibrotic tissue is formed during tissue ingrowth into interstices provided by the rough and/or porous surface of the remaining insoluble portion of coating 320. The resulting ingrown tissue promotes adequate anchoring and fixation of lead 110. Because the ingrown tissue includes modified fibrotic scar tissue, however, it is easier to separate lead 110 from the surrounding tissue by pulling and/or turning the lead 110 during removal. Stated differently, steroid release from the structure receiving tissue ingrowth on an insulating portion of elongate body 300 results in friable tissue ingrowth that is more easily disrupted or separated from lead 110 upon extraction and removal of lead 110. Thus, lead 110 offers advantages for both its fixation and removal. Furthermore, reduced pacing and defibrillation threshold energies may be obtained by providing the therapeutic agent near electrode regions, as discussed above.

In a further embodiment, coating 320 provides a therapeutic agent including more substantially soluble dexamethasone sodium phosphate particles. These particles are dispersed in a substantially insoluble medium, such as biocompatible silicone rubber medical adhesive, other polymer, or other suitable biocompatible adhesive substance. Silicone rubber medical adhesive is permeable by water vapor. As a result, water vapor can reach interior dry pockets of the dispersed soluble particles, allowing such particles to dissolve and be released from coating 320 into the surrounding tissue. Other biocompatible, water vapor permeable, and substantially insoluble adhesive or polymeric media can also be used.

In another embodiment, coating 320 provides a therapeutic agent including more substantially soluble dexamethasone sodium phosphate elements dispersed in the substantially insoluble silicone rubber medical adhesive. This embodiment advantageously provides both friable tissue encapsulation and osmotic swelling.

In yet another embodiment, smooth coating 320 includes a combination of the therapeutically active agents, such as dexamethasone acetate and dexamethasone sodium phosphate, dispersed in the substantially insoluble medium (e.g., silicone rubber). In this embodiment, upon exposure to bodily fluids, rapid initial release of the dexamethasone drug substance occurs predominantly in the form of the more soluble dexamethasone sodium phosphate. Release of the dexamethasone drug substance in the form of dexamethasone acetate also occurs upon exposure to bodily fluids, but does so more slowly. Dissolution and release of the dexamethasone sodium phosphate phase will also result in the development of porous surface structures into which tissue ingrowth can occur. Release of the combined forms of the steroid will also serve to modify the tissue ingrowth producing friable encapsulation.

In yet another embodiment, smooth coating 320 includes a combination of the therapeutically active agent dexamethasone acetate and a more substantially soluble nontherapeutic inert agent, such as mannitol or glycerol. In this embodiment, upon exposure to bodily fluids, both the active and inert agents dissolve. The more substantially soluble inert agent first aids in the initial implantation, by lowering lead friction and making the lead more slippery. Then the inert agent quickly dissolves to generate porous features on the surface of the lead body. Release of the dexamethasone drug substance in the form of dexamethasone acetate also occurs upon exposure to bodily fluids, but does so more slowly, as described above. Release of these combined forms of active and inert additives again serves to modify the tissue ingrowth, providing friable encapsulation.

During manufacture, at least one insulating portion of elongate body 300 is coated with coating 320. The coating 320 cures such that it adheres to elongate body 300. Increasing the percentage of soluble particles dispersed in the insoluble medium results in increased roughening and/or porosity after lead 110 is exposed to an aqueous substance during use. However, the percentage of soluble particles dispersed in the insoluble medium is typically not so great as to diminish the adhesive properties of coating 320 or to diminish the integrity of coating 320 after its partial dissolution during its use. In a first embodiment, coating 320 includes up to 40% soluble particles (e.g., dexamethasone, dexamethasone acetate or dexamethasone sodium phosphate) combined with or dispersed in the insoluble medium (e.g., silicone rubber medical adhesive). In a second embodiment, coating 320 includes up to 35% soluble particles (e.g., dexamethasone, dexamethasone acetate or dexamethasone sodium phosphate) combined with or dispersed in the insoluble medium (e.g., silicone rubber medical adhesive). In a third embodiment, coating 320 includes up to 30% soluble particles (e.g., dexamethasone, dexamethasone acetate or dexamethasone sodium phosphate) combined with or dispersed in the insoluble medium (e.g., silicone rubber medical adhesive). In a fourth embodiment, coating 320 includes between 30%–40% soluble particles (e.g., dexamethasone, dexamethasone acetate or dexamethasone sodium phosphate) combined with or dispersed in the insoluble medium (e.g., silicone rubber medical adhesive).

FIG. 4A is a schematic drawing illustrating generally, by way of example, but not by way of limitation, another embodiment of lead 110, which is similar in many respects to the embodiment of lead 110 described with respect to FIG. 3A. The embodiment of FIG. 4A includes a plurality of electrodes, such as ring electrodes 310A–C, and tip electrode 400 at distal end 140 of lead 110. The electrodes 310A–C and 400 are coupled to proximal end 135, such as by a corresponding plurality of conductors 305A–D interconnecting electrodes 310A–C and 400 to individual connectors 315 that are received at corresponding receptacles on device 105. Alternatively, one or more of electrodes 310A–C is tied to one or more others of electrodes 310A–C using one or more shared/common conductors 305A–D.

Interelectrode portions of insulating elongate body 300 of lead 110 are covered with coatings 320A–C, which are at least partially dissolved during use as described above, as illustrated in FIG. 4B. In one embodiment, coatings 320A–C elute steroids or other therapeutic agents during dissolution, as discussed above. In a further embodiment, one or more of coatings 320A–C also overlap one or more portions of one or more adjacent electrodes, providing an insulating covering that reduces the exposed surface area of the partially covered electrode. The embodiment of FIGS. 4A–B also optionally include one or more additional passive or active fixations devices, such as one or more tines 405A–B extending laterally outward from a portion of elongate body 300 at or near tip electrode 400. In one example, tines 405A–B are formed of the same insulating material as elongate body 300.

Figure 5A:
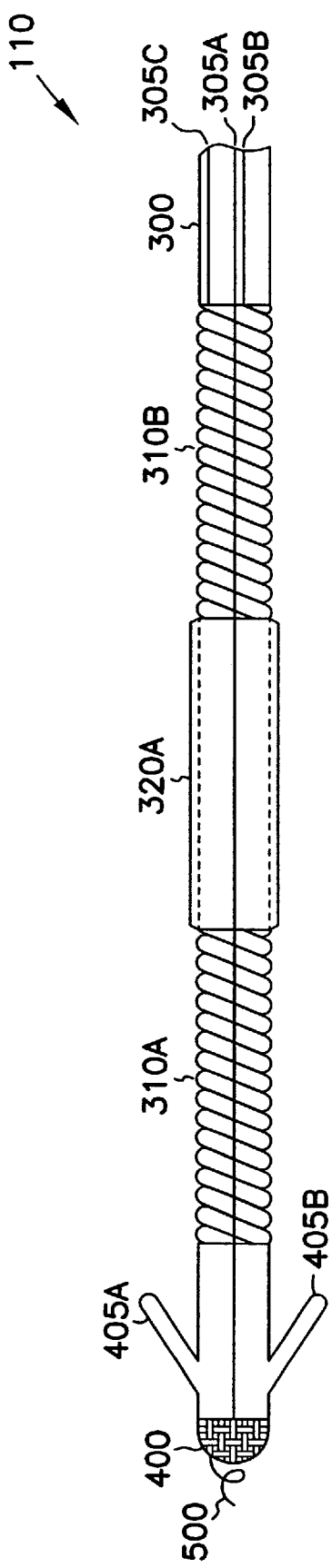
FIG. 5A is a schematic drawing illustrating a further embodiment of portions of a lead.
Figure 5B:
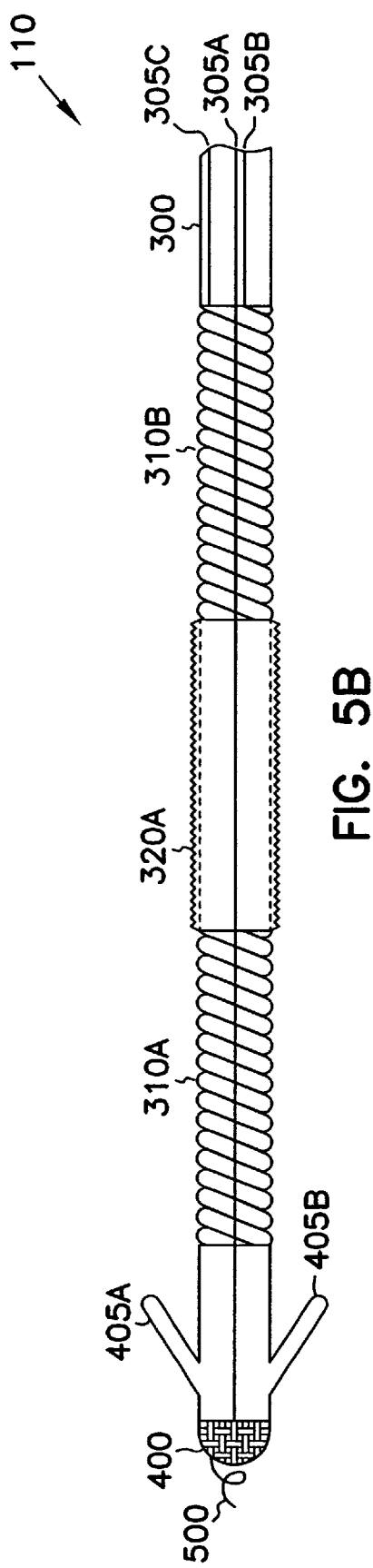
FIG. 5B is a schematic drawing illustrating the portions of the lead of FIG. 5A after exposure to an aqueous substance.

FIG. 5A is a schematic drawing illustrating generally, by way of example, but not by way of limitation, another embodiment of lead 110, which is similar in many respects to the embodiment of lead 110 described with respect to FIG. 4A. The embodiment of FIG. 5A includes one or more electrodes, such as coil electrodes 310A–B, which each include wires wound around the peripheral circumference of elongate body 300. Coil electrodes 310A–B provide a nonuniform, rough peripheral surfaces that allow tissue ingrowth into interstitial regions between the individual coil windings for providing improved fixation. Interelectrode coating 320A partially dissolves after implantation, as discussed above, which also allows tissue ingrowth into the substantially insoluble substrate portion of interelectrode coating 320A, as illustrated in FIG. 5B. In one embodiment, coating 320A releases a therapeutic agent during dissolution, such as a steroid that modifies the fibrotic scarring content of the tissue ingrowth into the rough/porous substrate portion of coating 320A. The steroid elution from coating 320A also modifies the fibrotic scar tissue content of the tissue that grows into the nearby interstices of electrodes 310A–B. The resulting ingrown tissue is friable. It provides fixation of lead 110, but allows easier lead extraction. In a further embodiment, coating 320A also overlaps one or more portions of one or more electrodes, providing an insulating covering that reduces the exposed surface area of the partially covered electrode. FIG. 5A also illustrates an embodiment of lead 110 that includes optional other fixation mechanisms, such as one or more of mesh tip electrode 400 or a helical anchor 500 extending longitudinally outward from tip electrode 400. It is understood that one or more of these or other like fixation mechanisms can be used either alone, or in combination with each other, as desired.

Figure 6:
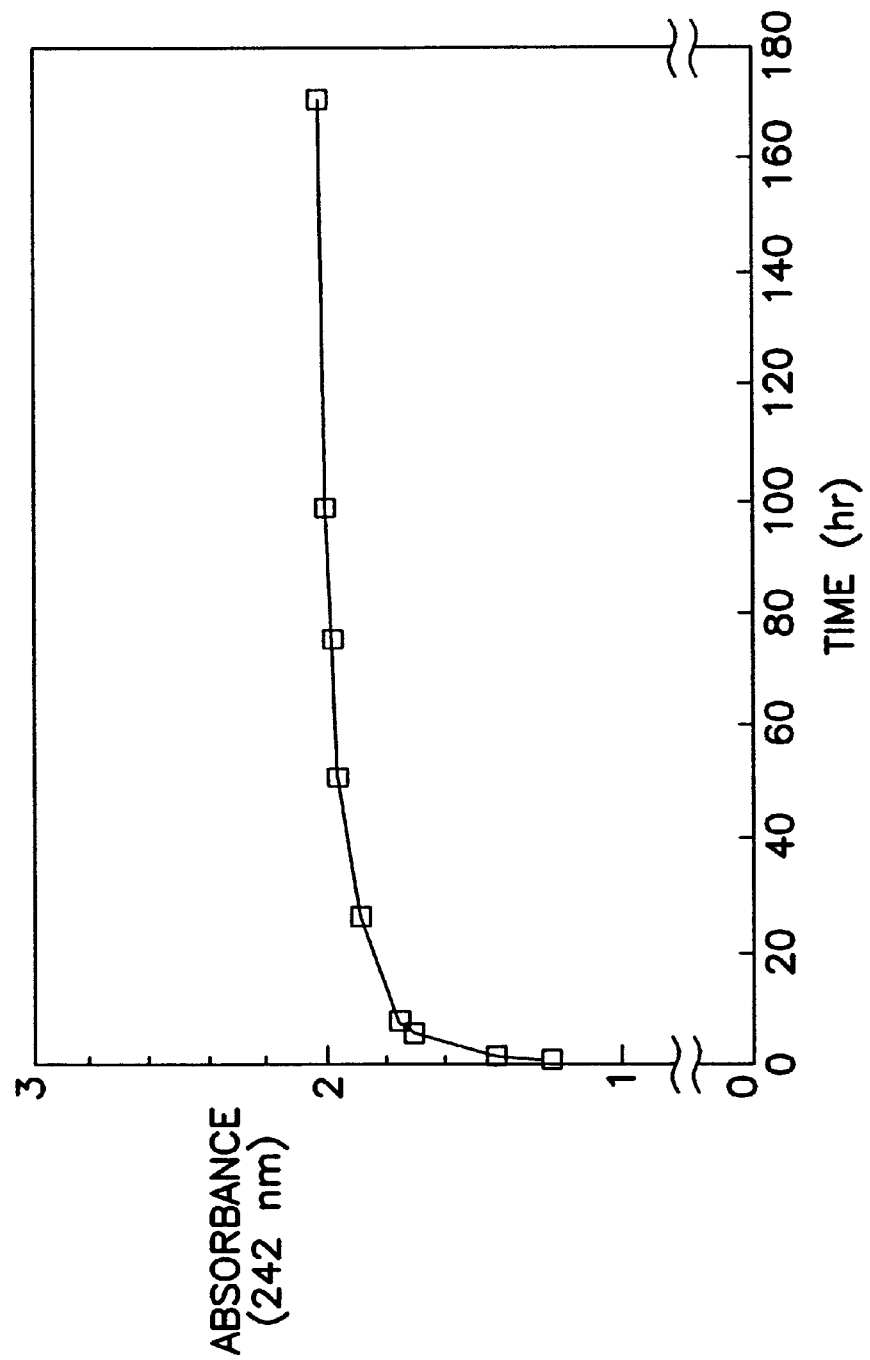
FIG. 6 is a graph of steroid absorbance vs. time, illustrating generally test results for a prototype embodiment of a lead.

FIG. 6 is a graph of steroid absorbance vs. time, illustrating generally, by way of example, but not by way of limitation, test results for a prototype embodiment of lead 110, which is similar to that illustrated in FIG. 4A, but including a single tip electrode and 4 ring electrodes. The electrodes were separated by polymeric interelectrode regions coated with silicone rubber medical adhesive that included approximately 10% dexamethasone acetate. Approximately 1.8 milligrams of dexamethasone acetate was released over a period of approximately one week, with some drug release still continuing at one week after exposure to an aqueous solution as indicated by the slight positive slope of the curve in FIG. 6 at that time. In one embodiment, the time period during which the therapeutic agent is released is optimized by proper selection of its aqueous solubility, or by otherwise selecting the appropriate combination of the substantially soluble therapeutic agent, the substantially insoluble binder medium, and an appropriate inert additive.

Conclusion

The above-described system provides, among other things, a cardiac rhythm management system providing an endocardial cardiac rhythm management lead with an at least partially dissolvable coating on insulating portions of the lead body at or near its distal end, which promotes tissue ingrowth to secure the lead in place. In one embodiment, dissolution of the coating releases a therapeutic agent. In a further embodiment, the therapeutic agent includes a steroid that modifies the fibrotic scar tissue content of tissue ingrowth, such that the resulting bond between the tissue and the lead is weak, such that the lead can be easily extracted if desired.

Although the present cardiac rhythm management system is described above with respect to a lead that is disposed within the vasculature of a coronary sinus and/or a great cardiac vein, it is understood that the endocardial lead can be positioned elsewhere within the heart, such as within the right or left atria or ventricles, within other blood vessels, or elsewhere.

It is to be understood that the above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

What is claimed is:

1. A device including:
    a device body at least partially covered by a peripheral surface; and
    an at least partially dissolvable coating at least partially on a portion of the peripheral surface of the device body, the coating providing at least one of a rough surface and a porous surface after being exposed to an aqueous substance.

2. The device of claim 1, in which the coating provides a substantially smooth surface before being exposed to the aqueous substance.

3. The device of claim 2, in which the coating includes a plurality of substantially soluble particles dispersed in a substantially insoluble medium.

4. The device of claim 3, in which the soluble particles include a therapeutic agent.

5. The device of claim 4, in which the therapeutic agent includes at least one of a drug, a steroid, a corticosteroid, an antibiotic, and an antirejection agent.

6. The device of claim 4, in which the therapeutic agent includes one of dexamethasone acetate and dexamethasone sodium phosphate.

7. The device of claim 3, in which the insoluble medium includes a biocompatible medical adhesive.

8. The device of claim 7, in which the medical adhesive includes silicone.

9. The device of claim 1, which the coating includes a therapeutic agent that promotes friable tissue associated with the portion of the peripheral surface of the device body for easier device removal.

10. The device of claim 1, in which the device body is an elongate body including a proximal and a distal end.

11. The device of claim 10, further including at least one elongate electrical conductor, having a proximal end and a distal end, the conductor carried within the elongate body and extending longitudinally along substantially the entire length between the proximal and distal ends of the elongate body, and in which the peripheral surface of the elongate body includes an insulating portion.

12. The device of claim 11, in which the coating includes a plurality of substantially soluble particles dispersed in a substantially insoluble medium, the insoluble medium adhered to the insulating portion of the elongate body.

13. The device of claim 11, further including at least one electrode located at or near the distal end of the elongate body, the electrode being coupled to the distal end of the conductor.

14. The device of claim 13, in which the coating also covers at least part of the at least one electrode.

15. The device of claim 11, in which the at least partially dissolvable coating is on the insulating portion of the peripheral surface at or near the distal end of the elongated body.

16. A device including:
    a flexible elongate body having a proximal and a distal end and a peripheral surface; and
    a partially dissolvable coating at least partially on a portion of the peripheral surface of the elongate body, the coating providing at least one of a rough surface, a porous surface, and a swollen surface after being exposed to an aqueous substance, the coating including a plurality of substantially soluble particles dispersed in a substantially insoluble silicone adhesive that is bonded to the elongate body, and in which the substantially soluble particles are selected from the group consisting of dexamethasone, dexamethasone acetate and dexamethasone sodium phosphate.

17. The device of claim 16, in which the coating includes up to 40% substantially soluble particles dispersed in the adhesive.

18. The device of claim 16, in which the coating includes up to 35% substantially soluble particles dispersed in the adhesive.

19. The device of claim 16, in which the coating includes up to 30% substantially soluble particles dispersed in the adhesive.

20. The device of claim 17, further including a plurality of electrodes located at or near the distal end of the elongate body, each electrode being coupled to the distal end of at least one of the conductors.

21. The device of claim 20, in which the coating also covers at least part of at least one of the electrodes.

22. The device of claim 16, further including a plurality of elongate electrical conductors, each conductor having a proximal end and a distal end, each conductor carried within the elongate body and extending longitudinally along substantially the entire length between the proximal and distal ends of the elongate body, of which the peripheral surface includes an insulating portion.

23. A device including:
    a flexible elongate body having a proximal and a distal end and a peripheral surface; and
    an at least partially-dissolvable means for coating a portion of the peripheral surface at or near the distal end of the elongate body, providing at least one of a rough surface, a porous surface, and a swollen surface, after being exposed to an aqueous substance, for fixation of tissue thereto.

24. The device of claim 23, further including a plurality of elongate electrical conductors, each conductor having a proximal end and a distal end, each conductor carried within the elongate body and extending longitudinally along substantially the entire length between the proximal and distal ends of the elongate body, of which the peripheral surface includes an insulating portion.

25. The device of claim 24, further including a plurality of electrodes located at or near the distal end of the elongate body, each electrode being coupled to the distal end of at least one of the conductors.

26. The device of claim 25, in which the means for coating includes a means for coating at least part of at least one of the electrodes.

27. A method including:
    implanting an implantable medical device;
    exposing the an implantable medical device to an aqueous substance; and
    partially dissolving a coating at least partially on a portion of the implantable medical device to provide at least one of a rough surface, a porous surface, and a swollen surface, thereby promoting tissue ingrowth.

28. The method of claim 27, in which partially dissolving the coating includes releasing a therapeutic agent.

29. The method of claim 28, in which releasing the therapeutic agent includes releasing at least one of a drug, a steroid, a corticosteroid, an antibiotic, and an antirejection agent.

30. The method of claim 28, in which releasing the therapeutic agent includes releasing at least one of dexamethasone, dexamethasone acetate, and dexamethasone sodium phosphate.

31. The method of claim 27, in which dissolving the coating includes releasing a therapeutic agent that promotes friable tissue associated with the portion of the implantable medical device for easier device removal.

32. The method of claim 27, in which the implanting the implantable medical device includes disposing a cardiac rhythm management lead.

33. The method of claim 27, in which disposing the lead includes translumenally disposing the lead in at least one of a right atrium and a right ventricle of the heart.

34. The method of claim 27, in which disposing the lead includes translumenally disposing the lead in at least one of a coronary sinus and a great cardiac vein of the heart.

35. A method comprising:
covering at least a portion of an implantable medical device with an insulating peripheral surface; and
coating at least a portion of the insulating peripheral surface with an at least partially dissolvable coating, the coating providing at least one of a rough surface, a porous surface, and a swollen surface after being exposed to an aqueous substance.

36. The method of claim 35, in which coating includes applying a medium carrying soluble elements.

37. The method of claim 36, in which coating further includes applying biocompatible silicone adhesive carrying a steroid.

38. The method of claim 36, in which coating further includes applying biocompatible silicone adhesive including at least one of dexamethasone, dexamethasone acetate, and dexamethasone sodium phosphate.

39. The method of claim 36, in which coating includes applying biocompatible silicone adhesive including up to 40% of at least one of dexamethasone, dexamethasone acetate, and dexamethasone sodium phosphate.

40. The method of claim 36, in which coating includes applying biocompatible silicone adhesive including up to 35% of at least one of dexamethasone, dexamethasone acetate, and dexamethasone sodium phosphate.

41. The method of claim 36, in which coating includes applying biocompatible silicone adhesive including up to 30% of at least one of dexamethasone, dexamethasone acetate, and dexamethasone sodium phosphate.

42. The method of claim 36, in which coating includes applying biocompatible silicone adhesive including between 30% and 40% of at least one of dexamethasone, dexamethasone acetate, and dexamethasone sodium phosphate.

43. The method of claim 35, further including forming at least an electrode coupled to the implantable medical device.

44. The method of claim 43, further including coating a portion of the electrode with the at least partially dissolvable coating.

45. The method of claim 35, in which coating at least a portion of the insulating peripheral surface includes providing a therapeutic agent that, upon at least partial dissolution of the coating, provides friable tissue associated with the insulating peripheral surface of the implantable medical device for easier device removal.

46. A device including:
a device body at least partially covered by a peripheral surface; and
an at least partially dissolvable coating at least partially on a portion of the peripheral surface of the device body, the coating providing a rough surface after being exposed to an aqueous substance.

47. A device including:
a device body at least partially covered by a peripheral surface; and
an at least partially dissolvable coating at least partially on a portion of the peripheral surface of the device body, the coating providing a porous surface after being exposed to an aqueous substance.

48. A device including:
a flexible elongate body having a proximal and a distal end and a peripheral surface; and
a partially dissolvable coating at least partially on a portion of the peripheral surface of the elongate body, the coating providing a rough surface after being exposed to an aqueous substance, the coating including a plurality of substantially soluble particles dispersed in a substantially insoluble silicone adhesive that is bonded to the elongate body, and in which the substantially soluble particles are selected from the group consisting of dexamethasone, dexamethasone acetate and dexamethasone sodium phosphate.

49. A device including:
a flexible elongate body having a proximal and a distal end and a peripheral surface; and
a partially dissolvable coating at least partially on a portion of the peripheral surface of the elongate body, the coating providing a porous surface after being exposed to an aqueous substance, the coating including a plurality of substantially soluble particles dispersed in a substantially insoluble silicone adhesive that is bonded to the elongate body, and in which the substantially soluble particles are selected from the group consisting of dexamethasone, dexamethasone acetate and dexamethasone sodium phosphate.

50. A device including:
a flexible elongate body having a proximal and a distal end and a peripheral surface; and
a partially dissolvable coating at least partially on a portion of the peripheral surface of the elongate body, the coating providing a swollen surface after being exposed to an aqueous substance, the coating including a plurality of substantially soluble particles dispersed in a substantially insoluble silicone adhesive that is bonded to the elongate body, and in which the substantially soluble particles are selected from the group consisting of dexamethasone, dexamethasone acetate and dexamethasone sodium phosphate.

51. A device including:
a flexible elongate body having a proximal and a distal end and a peripheral surface; and
an at least partially-dissolvable means for coating a portion of the peripheral surface at or near the distal end of the elongate body, providing a rough surface after being exposed to an aqueous substance, for fixation of tissue thereto.

52. A device including:
a flexible elongate body having a proximal and a distal end and a peripheral surface; and
an at least partially-dissolvable means for coating a portion of the peripheral surface at or near the distal end of the elongate body, providing a porous surface after being exposed to an aqueous substance, for fixation of tissue thereto.

53. A device including:

a flexible elongate body having a proximal and a distal end and a peripheral surface; and an at least partially-dissolvable means for coating a portion of the peripheral surface at or near the distal end of the elongate body, providing a swollen surface, after being exposed to an aqueous substance, for fixation of tissue thereto.

54. A method including:

implanting an implantable medical device;

exposing the an implantable medical device to an aqueous substance; and partially dissolving a coating at least partially on a portion of the implantable medical device to provide a rough surface, thereby promoting tissue ingrowth.

55. A method including:

implanting an implantable medical device;

exposing the an implantable medical device to an aqueous substance; and partially dissolving a coating at least partially on a portion of the implantable medical device to provide a porous surface, thereby promoting tissue ingrowth.

56. A method including:

implanting an implantable medical device;

exposing the an implantable medical device to an aqueous substance; and partially dissolving a coating at least partially on a portion of the implantable medical device to provide a swollen surface, thereby promoting tissue ingrowth.

57. A method comprising:

covering at least a portion of an implantable medical device with an insulating peripheral surface; and coating at least a portion of the insulating peripheral surface with an at least partially dissolvable coating, the coating providing a rough surface after being exposed to an aqueous substance.

58. A method comprising:

covering at least a portion of an implantable medical device with an insulating peripheral surface; and coating at least a portion of the insulating peripheral surface with an at least partially dissolvable coating, the coating providing at least one of a porous surface after being exposed to an aqueous substance.

59. A method comprising:

covering at least a portion of an implantable medical device with an insulating peripheral surface; and coating at least a portion of the insulating peripheral surface with an at least partially dissolvable coating, the coating providing a swollen surface after being exposed to an aqueous substance.

* * * * *

UNITED STATES PATENT AND TRADEMARK OFFICE
CERTIFICATE OF CORRECTION

PATENT NO. : 6,584,363 B2
DATED : June 24, 2003
INVENTOR(S) : Ronald W. Heil, Jr., John E. Heil and Randy Westlund It is certified that error appears in the above-identified patent and that said Letters Patent is hereby corrected as shown below:

Column 10,
Line 23, delete "claim 17" and insert -- claim 19 -- therefor.

Column 11,
Lines 18 and 21, delete "claim 27" and insert -- claim 32 -- therefor.

Signed and Sealed this

Twenty-third Day of December, 2003

JAMES E. ROGAN
*Director of the United States Patent and Trademark Office*